(12) United States Patent
Shoseyov et al.

(10) Patent No.: US 11,957,721 B2
(45) Date of Patent: Apr. 16, 2024

(54) EDIBLE PLANT PARTS ENRICHED WITH PROBIOTIC BACTERIA

(71) Applicants: YISSUM RESEARCH DEVELOPMENT COMPANY OF THE HEBREW UNIVERSITY OF JERUSALEM LTD., Jerusalem (IL); OFEK—ESHKOLOT RESEARCH AND DEVELOPMENT LTD., Karmiel (IL)

(72) Inventors: Oded Shoseyov, Shoham (IL); Sigal Baruch-Sharon, Ness-Ziona (IL); Betty Schwartz, Rehovot (IL); Lilach Iasur Kruh, Kibbutz Afek (IL); Roni Almon, Timrat (IL); Alaa Naama-Amar, Dier Al-Assad (IL)

(73) Assignees: YISSUM RESEARCH DEVELOPMENT COMPANY OF THE HEBREW UNIVERSITY OF JERUSALEM LTD., Jerusalem (IL); OFEK—ESHKOLOT RESEARCH AND DEVELOPMENT LTD., Karmiel (IL)

( * ) Notice: Subject to any disclaimer, the term of this patent is extended or adjusted under 35 U.S.C. 154(b) by 53 days.

(21) Appl. No.: 17/046,103

(22) PCT Filed: Apr. 10, 2019

(86) PCT No.: PCT/IL2019/050403
§ 371 (c)(1),
(2) Date: Oct. 8, 2020

(87) PCT Pub. No.: WO2019/198079
PCT Pub. Date: Oct. 17, 2019

(65) Prior Publication Data
US 2021/0030819 A1 Feb. 4, 2021

Related U.S. Application Data

(60) Provisional application No. 62/655,819, filed on Apr. 11, 2018.

(51) Int. Cl.
| | | |
|---|---|---|
| A61K 35/745 | (2015.01) |
| A23L 33/105 | (2016.01) |
| A23L 33/135 | (2016.01) |
| A61K 8/99 | (2017.01) |
| A61K 9/00 | (2006.01) |
| A61K 35/741 | (2015.01) |
| A61K 35/742 | (2015.01) |
| A61K 35/747 | (2015.01) |
| A61P 1/12 | (2006.01) |
| A61P 1/14 | (2006.01) |

(52) U.S. Cl.
CPC .......... *A61K 35/745* (2013.01); *A23L 33/105* (2016.08); *A23L 33/135* (2016.08); *A61K 8/99* (2013.01); *A61K 9/0053* (2013.01); *A61K 35/741* (2013.01); *A61K 35/742* (2013.01); *A61K 35/747* (2013.01); *A61P 1/12* (2018.01); *A61P 1/14* (2018.01)

(58) Field of Classification Search
CPC ................................................... A23L 33/135
See application file for complete search history.

(56) References Cited

U.S. PATENT DOCUMENTS

| 4,960,814 A | 10/1990 | Wu |
| 5,025,004 A | 6/1991 | Wu |
| 9,144,588 B2 | 9/2015 | Rubio |

FOREIGN PATENT DOCUMENTS

| JP | 2006034262 A | 2/2006 |
| JP | 2009100677 A | 5/2009 |
| JP | 2017099373 A | 6/2017 |
| JP | 2019024388 A | 2/2019 |
| KR | 20140087517 A | 7/2014 |
| WO | 2014046553 A1 | 3/2014 |
| WO | 2018050739 A1 | 3/2018 |

OTHER PUBLICATIONS

Alegre, I. et al., "Microbiological and physicochemical quality of fresh-cut apple enriched with the probiotic strain Lactobacillus rhamnosus GG", Food Microbiology, vol. 28, pp. 59-66. (Year: 2011).*
Betoret, et al. "Development of probiotic-enriched dried fruits by vacuum impregnation", Journal of Food Engineering, vol. 56, pp. 273-277. (Year: 2003).*
Rößle et al. "Evaluation of fresh-cut apple slices enriched with probiotic bacteria", Innovative Food Science and Emerging Technologies, vol. 11, pp. 203-209. (Year: 2010).*
Macey, Bobby. "Which Apple Is The Healthiest For You?", SelectHealth, https://selecthealth.org/blog/2016/07/healthiest-apple (Accessed: Jul. 2022) (Year: 2016).*
Rößle et al. "Development of potentially synbiotic fresh-cut apple slices", Journal of Functional Foods, vol. 2, pp. 245-254. (Year: 2010).*
Bai, et al., "Coating selection for 'Delicious' and other apples", Postharvest Biology and Technology, vol. 28, pp. 381-390. (Year: 2003).*
Trias et al., "Bioprotection of Golden Delicious apples and Iceberg lettuce against foodborne bacterial pathogens by lactic acid bacteria", International Journal of Food Microbiology, vol. 123, pp. 50-60. (Year: 2008).*

(Continued)

*Primary Examiner* — Michelle F. Paguio Frising
*Assistant Examiner* — Grant C Currens
(74) *Attorney, Agent, or Firm* — The Roy Gross Law Firm, LLC; Roy Gross

(57) ABSTRACT

The present invention relates to edible plant parts or tissues comprising probiotic bacteria and use thereof for oral delivery of the probiotic bacteria to an organism and enriching and/or improving the organism gastrointestinal tract microbiome. The present invention further relates to methods for selecting and/or producing probiotic bacteria capable of colonizing a plant tissue.

19 Claims, 7 Drawing Sheets

(56) References Cited

OTHER PUBLICATIONS

Avram-Hananel et al., (2010) E durans strain M4-5 isolated from human colonic flora attenuates intestinal Inflammation. Dis Colon Rectum 53(12): 1676-1686.

Bäckhed et al., (2012) Defining a healthy human gut microbiome: current concepts, future directions, and clinical applications. Cell Host Microbe 12(5): 611-622.

Balamuralidhara et al., (2011) pH sensitive drug delivery systems: a review. Am J Drug Discov Dev 1: 24-48.

Beattie and Lindow (1999) Bacterial colonization of leaves: a spectrum of strategies. Phytopathology 89(5): 353-359.

Berg G., Erlacher A., Grube M. (2015) The Edible Plant Microbiome: Importance and Health Issues. In: Lugtenberg B. (eds) Principles of Plant-Microbe Interactions. Springer, Cham. https://doi.org/10.1007/978-3-319-08575-3_44. pp. 419-426.

Bertz et al., (2013) Encapsulation of proteins in hydrogel carrier systems for controlled drug delivery: influence of network structure and drug size on release rate. J Biotechnol 163(2): 243-249.

Biedrzycka (2004) Microecosystem of the large intestine as a target-place for probiotics and prebiotics used as functional compounds of diet—a review. Polish Journal of Food and Nutrition Sciences 13/54(2): 143-150.

Bozdag et al., (1999) Formulation and stability evaluation of enteric-coated omeprazole formulations. S.T.P. Pharma Sciences 9(4): 321-327.

Caillard et al., (2016) Characterization of a food-based enteric coating for capsules and its compatibility with an alternative sealing method. Int J Pharm 499(1-2): 321-329.

Chassaing et al., (2015) Dietary emulsifiers impact the mouse gut microbiota promoting colitis and metabolic syndrome. Nature. Author manuscript; available in PMC Jun. 16, 2016. Published in final edited form as: Nature. Mar. 5, 2015; 519(7541): 92-96. 37 pages.

Croes et al., (2013) Bacterial communities associated with Brassica napus L. grown on trace element-contaminated and non-contaminated fields: a genotypic and phenotypic comparison. Microb Biotechnol 6(4): 371-384.

Fijan (2014) Microorganisms with claimed probiotic properties: an overview of recent literature. Int J Environ Res Public Health 11(5): 4745-4767.

Franz et al., (2011) Enterococci as probiotics and their implications in food safety. Int J Food Microbiol 151(2): 125-140.

Fricke (2014) The more the merrier? Reduced fecal microbiota diversity in preterm infants treated with antibiotics. J Pediatr 165(1): 8-10.

Grajek et al., (2005) Probiotics, prebiotics and antioxidants as functional foods. Acta Biochimica Polonica 52(3): 665-671. Presented at the International Review Conference on Biotechnology, Vienna, Austria, Nov. 2004.

Hodge (1944) The chronic toxicity of cellulose acetate phthalate in rats and dogs. Journal of Pharmacology and Experimental Therapeutics 80(3): 250-255.

Human Microbiome Project Consortium (2012) Structure, function and diversity of the healthy human microbiome. Nature 486(7402): 207-214.

Indira Devi S., Momota P. (2015) Plant-Endophyte Interaction and Its Unrelenting Contribution Towards Plant Health. In: Arora N. (eds) Plant Microbes Symbiosis: Applied Facets. Springer, New Delhi. http://doi-org-443.webvpn.fjmu.edu.cn/10.1007/978-81-322-2068-8_7. pp. 147-162.

Johansson M.E.V., Hansson G.C. (2012) Preservation of Mucus in Histological Sections, Immunostaining of Mucins in Fixed Tissue, and Localization of Bacteria with FISH. In: McGuckin M., Thornton D. (eds) Mucins. Methods in Molecular Biology (Methods and Protocols), vol. 842. Humana Press. https://doi.org/10.1007/978-1-61779-513-8_13. pp. 229-235.

Kamnev et al., (2005) Effects of heavy metals on plant-associated rhizobacteria: comparison of endophytic and non-endophytic strains of Azospirillum brasilense. J Trace Elem Med Biol 19(1): 91-95.

Kõiv et al., (2019) Endophytic bacterial communities in peels and pulp of five root vegetables. PLoS One 14(1): 0210542; 17 pages.

Lozupone et al., (2012) Diversity, stability and resilience of the human gut microbiota. Nature 489(7415): 220-230.

Murugappan et al., (2013) Symbiotic influence of endophytic Bacillus pumilus on growth promotion and probiotic potential of the medicinal plant Ocimum sanctum. Symbiosis 60: 91-99.

Ouwehand et al., (1999) Probiotics: mechanisms and established effects. International Dairy Journal 9(1): 43-52.

Peykov et al., (2012) Rapid identification of Enterococcus faecalis by species-specific primers based on the genes involved in the Entner-Doudoroff pathway. Mol Biol Rep 39(6): 7025-7030.

Puupponen-Pimia et al., (2002) Development of functional ingredients for gut health. Trends in Food Science & Technology 13(1): 3-11.

Qvit-Raz et al., (2008) Drop-size soda lakes: transient microbial habitats on a salt-secreting desert tree. Genetics 178 (3): 1615-1622.

Richter-Heitmann et al., (2016) Evaluation of Strategies to Separate Root-Associated Microbial Communities: A Crucial Choice in Rhizobiome Research. Front Microbiol 7: 773; 11 pages.

Ringel et al., (2012) Using Probiotics in Gastrointestinal Disorders. The American Journal of Gastroenterology Supplements 1(1): 34-40.

Ryan et al., (2008) Bacterial endophytes: recent developments and applications. FEMS Microbiol Lett 278(1): 1-9.

Sachdeva et al., (2016) Development and characterization of enteric-coated microparticles of biochanin A for their beneficial pharmacological potential in estrogen deficient-hypertension. Drug Deliv 23(6): 2044-2057.

Song et al., (2014) Preparation and Control Efficiency of Seed Coating Agent by Antagonistic Actinomycetes Against Clubroot. Journal of Agricultural Science 6(3): 132-139.

Wong et al., (2017) In-vitro evaluation of enteric coated insulin tablets containing absorption enhancer and enzyme Inhibitor. J Pharm Pharmacol 69(3): 285-294.

Ziemer and Gibson (1998) An Overview of Probiotics, Prebiotics and Synbiotics in the Functional Food Concept: Perspectives and Future Strategies. International Dairy Journal 8(5-6): 473-479.

Betoret N. et al: "Development of probiotic-enriched dried fruits by vacuum impregnation", Journal of Food Engineering, 2003, vol. 56, issues 2-3, pp. 273-277. https://doi.org/10.1016/S0260-8774(02)00268-6.

Roessle C. et al: "Evaluation of fresh-cut apple slices enriched with probiotic bacteria", Innovative Food Science and Emerging Technologies, 2010, vol. 11, pp. 203-209. DOI:10.1016/J.IFSET.2009.08.016.

PCT International Search Report for International Application No. PCT/IL2019/050403, dated Sep. 20, 2019, 6pp.

PCT Written Opinion for International Application No. PCT/IL2019/050403, dated Sep. 20, 2019, 10pp.

PCT International Preliminary Report on Patentability for International Application No. PCT/IL2019/050403, dated Oct. 13, 2020, 11pp.

* cited by examiner

EDIBLE PLANT PARTS ENRICHED WITH PROBIOTIC BACTERIA

FIELD OF THE INVENTION

The present invention relates to edible plant tissue enriched with probiotic bacteria and use thereof for oral delivery of the probiotic bacteria to an organism and enriching and/or improving the organism gastrointestinal tract microbiome. The present invention further relates to methods for selecting and/or producing probiotic bacteria capable of colonizing a plant tissue.

BACKGROUND OF THE INVENTION

The human microbiota is the microbial community best described as "the sum of all microbial life living in or on the human body (Fricke, W. F. et al. J. Pediatr. 165, 8-10, 2014). It is an entity that has wide-reaching metabolic, nutritional, and immunological effects on the host, and as such has generated an interest within the biomedical research community. The microbiome evolves within a healthy host from birth to death, maintaining a homeostatic balance with the host's immune system. Healthy adult humans each typically harbor more than 1000 species of bacteria belonging to a relatively few known bacterial phyla with Bacteroidetes and Firmicutes being the dominant phyla (Catherine A. et al., Nature 489, 220-230, 2012). The microbiota of the gut is quite diverse compared to other body sites, and there is considerable variation in the constituents of the gut microbiota among apparently healthy individuals (Human Microbiome Project Consortium. Nature 486, 207-14, 2012). Recently, the Human Microbiome Project (HMP) reported a profound insight into the role of the microbiota in human health. For example, gut microbes train the immune system, protect against opportunistic pathogens, harvest nutrients and energy from diet, and ferment non-digestible carbohydrates. The disruption of the normal gut microbiota (dysbiosis) is associated with obesity, diabetes, various inflammatory bowel diseases (IBD) and autoimmune diseases. Many factors, either endogenous or exogenous, affect the composition of the gut microbiota. Endogenous factors include the host genotype, age, sex and both the adaptive and innate immune system. Exogenous factors include diet, exposure to medications and toxins, and illness, while diet exerts the largest impact on the gut microbiota.

Probiotics are live microorganisms, that, when administered in adequate amounts, confer a health benefit on the host (Backhed, F. et al. Cell Host Microbe 12, 611-622, 2012). In recent decades, probiotics have been studied as a means to modulate microbial populations and functions in order to promote health and prevent or manage intestinal disorders (Ringel, Y. et al., Am. J. Gastroenterol. Suppl. 1, 34-40, 2012). Accumulated data from clinical trials indicate that certain intestinal disease conditions associated with intestinal dysbiosis, e.g. antibiotic-associated diarrhea, necrotizing enterocolitis (NEC), ulcerative colitis, inflammatory bowel syndrome (IBS) and pouchitis, have yielded clinical benefits with some probiotic interventions. Probiotics largely act directly or indirectly on the intestinal microbiota; thus, it can be assumed that some probiotics correct or reduce the effect of dysbiosis. To achieve a probiotic status, microorganisms must fulfill a number of criteria related to safety, functional effects and technological properties. Some selected strains of *Lactobacillus, Bifidobacterium, Streptococcus, Lactococcus* and *Saccharomyces* have been promoted in food products because of their reputed health benefits (Ziemer, C. J. and Gibson, G. R., Int. Dairy J. 8, 473-479, 1998; Puupponen-Pimiä, R. et al., Trends Food Sci. Technol. 13, 3-11, 2002).

Plants are a basic and substantial part of human daily diet. Vegetables, fruit, herbs, nuts, and medicinal herbs belong to the raw-eaten plant parts. Human food thus comprises all parts of plants including associated microorganisms that can be colonized by up to $10^4$-$10^{10}$ microorganisms per gram of plant. These microbial populations inhabit different habitats throughout the plant organs including the phyllosphere (lettuce, cabbage), the rhizosphere (carrots, turnip), the carposphere (tomato, banana), as well as the seeds (beans, peas) and corresponding endospheres (Berg, G. et al., in: Principles of Plant-Microbe Interactions 419-426, Springer International Publishing, 2015. doi:10.1007/978-3-319-08575-3_44).

Endophytes are plant-endosymbiotic group of microorganisms, often bacteria or fungi. Endophytic bacteria colonize the internal tissues of plants showing no external sign of infection or negative effect on their host. The population of endophytes in a plant species is highly variable and depends on various components including, e.g., host species, host developmental stage, inoculum density and environmental condition. A distinction can be made between obligate endophytes (Croes, S. et al., Microb. Biotechnol. 6, 371-384, 2013) and facultative endophytes (Kamnev, A. A. et al., J. Trace Elem. Med. Biol. 19, 91-95, 2005). Obligate endophytes are being transmitted from the host plant to its seed; however, facultative endophytes spend only part of their life cycle in the inner tissue of plants. These endophytes enter the plant through different points including tissue wounds, stomata (pores found in the epidermis of leaves), lenticels (raised pores in the stems of woody plants), root cracks, and germinating radicals (the part of the embryo that develops into the root system). In addition, active penetration may be enabled by the secretion of pectolytic enzymes. Next, the endophytes inhabit the plant tissue either intercellular or through the vascular tubes. As mentioned above, endophytes seem to be ubiquitous in plant tissues, having been isolated from various parts of plants like flowers, fruits, leaves, stem, root, and seeds in various plant species (Indira Devi, S. and Momota, P. in Plant Microbes Symbiosis: Applied Facets 147-162, Springer India, 2015. doi:10.1007/978-81-322-2068-8_7).

Several species of plant endophytic bacteria have been suggested to have gut probiotic properties. For example, *Bacillus pumilus* isolated from tissues of the medicinal plant *Ocimum sanctum* exhibited probiotic properties such as acid tolerance, bile salt tolerance, auto-aggregation, antibiotic resistance and the absence of haemolytic activity (Murugappan R M et al., Symbiosis 60, 91-99, 2013, DOI 10.1007/s13199-013-0244-0). Deep sequencing of a 16S rRNA gene fragment and bacterial cultivation were used to characterize the microbiomes of five plant species with edible roots revealed the presence of lactic bacteria on the pulp of Topinambur (Jerusalem artichoke, *Helianthus tuberosus*) (Kõiv V et al., Plos One doi.org/10.1371/journal.pone.0210542 Jan. 11, 2019). U.S. Pat. No. 9,144,588 discloses biologically pure cultures of *Bacillus subtilis* isolated from the pericarp of nixtamalized corn, which produce peptides having antimicrobial activity. The *Bacillus* microorganisms may be included in probiotic food compositions to help maintain healthy gastrointestinal flora and modulate animal digestion.

Fully utilizing the beneficial effects attributed to probiotics requires maintaining the probiotic microorganism viability during the production of oral formulations and providing gastric protection to minimize losses of viability during the transit through the stomach. Thus, there is a great need for and it would be highly advantageous to have a vehicle for delivery of probiotics answering these needs.

SUMMARY OF THE INVENTION

The present invention provides a platform technology for producing a superior delivery vehicle of probiotic bacteria conferring a beneficial health effect on a host animal subject. The delivery vehicle is plant-based, combining highly efficient delivery of the beneficial probiotic bacteria to their site of action with the nutritional and health-promoting components of plant produce, particularly fresh plant produce.

The technology of the present invention is based in part on the unexpected discovery that bacteria known to have probiotic effect on animal subjects can be habituated to colonize plant tissues in significant amounts and in viable form. Typically, the probiotic bacteria are habituated by selection and direct evolution and/or enrichment processes. The present invention thus provides an edible plant part or tissue enriched with probiotic bacteria colonized therein and its use for oral delivery of the bacteria. The edible plant part colonized with probiotic bacteria of the present invention is advantageous over hitherto known microbiotic delivery vehicles as, in addition to protecting the bacteria from non-favorable environmental conditions, the edible plant part by itself has high nutritional values. Edible plant tissues are rich in non-digestible or low-digestible food ingredients that benefit the animal host (prebiotics), dietary fibers, and micro- and macro-nutrients. The combination of probiotic bacteria and prebiotic characteristics of the edible plant tissue (called "synbiotics") results in a synergic effect that selectively stimulates the growth of the probiotic bacterial community and promotes its activity in gastrointestinal tract of non-ruminant animals, specifically humans. Typically, the edible plant part is used as a fresh produce. The plant tissues provide the probiotic bacteria with suitable conditions for colonization, such that the probiotic bacteria are kept in a viable, preferably propagating form, such that high quantity of high-quality probiotic bacteria is delivered to the subject. Consequently, the probiotic bacteria are capable of affecting the structure and/or function of the recipient gastrointestinal bacterial population that is at least maintained healthy or improved to a healthier state. The plant tissue further provides protection to the probiotic bacteria from harsh environmental conditions and thus prolonging the shelf life of the bacteria. The edible plant part may be further coated with agents providing for a delayed release of the probiotic bacteria, particularly enteric coating agent(s) protecting the colonized probiotic bacteria from the acidic pH of the stomach.

According to one aspect, the present invention provides an edible plant part or a tissue derived therefrom enriched with probiotic bacteria of at least one species colonizing the edible plant part or tissue derived therefrom, wherein the probiotic bacteria are capable of inhabiting the gastrointestinal (GI) tract of an animal.

According to certain embodiments, the edible plant part or tissue derived therefrom comprises at least $10^4$ colony forming units (CFU) of the probiotic bacteria per gram of the edible plant part or tissue derived therefrom.

According to certain embodiments, at least 80% by weight of the edible plant part or tissue derived therefrom comprises at least $10^5$ CFU of the probiotic bacteria per gram of the edible plant part or tissue derived therefrom.

According to certain embodiments, at least 80% by weight of the edible plant part or tissue derived therefrom comprises at least $10^6$ CFU of the probiotic bacteria per gram of the edible plant part or tissue derived therefrom.

According to certain embodiments, the at least one probiotic bacteria species comprises at least 15% of the total bacteria species colonizing the edible plant part or tissue derived therefrom.

According to certain embodiments, the probiotic bacteria are present at a site selected from the group consisting of the edible plant part or tissue intercellular space the edible plant part or tissue intracellular space, and a combination thereof. According to certain embodiments, the probiotic bacteria are further present on the edible plant part or tissue surface. According to certain exemplary embodiments, the probiotic bacteria are colonized within the intercellular and intracellular space. According to additional exemplary embodiments, the probiotic bacteria are present in the intercellular space, the intracellular space and the surface of the edible plant part or tissue.

According to certain exemplary embodiments, the at least one probiotic bacteria species is a non-endophytic species, not previously demonstrated to colonize plant tissues.

According to certain embodiments, the at least one probiotic bacteria species is an endophytic species capable of naturally colonizing a plant. According to these embodiments, the concentration of the enriched probiotic bacteria in the edible plant part or tissue is higher compared to the concentration of the same probiotic bacteria in a corresponding edible plant part of a control plant. The control plant is a plant to which the probiotic bacteria were not intentionally applied at any growth stage. The control plant may harbor naturally occurring probiotic bacteria without the intervention according to the present invention.

It is to be explicitly understood that any probiotic bacterial species capable of surviving and/or proliferating in and/or on a plant tissue after been intentionally applied directly or indirectly is encompassed within the teachings of the present invention.

The CFU of the at least one probiotic bacterial cell can be in an active state or in a dormant state.

According to certain embodiments, the CFU of the at least one probiotic bacterial species is an active bacterial cell. According to other embodiments, the CFU is in a dormant state selected from the group consisting of a spore, a cyst and a resting-cells. According to other exemplary embodiments, the CFU of the at least one probiotic bacterial species is in a dormant form of a spore.

According to another aspect, the present invention provides a plurality of edible plant parts or tissues derived therefrom, wherein at least 80% of the plurality of edible plant parts is enriched with probiotic bacteria of at least one species colonizing the edible plant part or tissue derived therefrom, wherein the probiotic bacteria are capable of inhabiting the gastrointestinal (GI) tract of an animal.

The edible plant part enriched with probiotic bacteria is as described hereinabove.

Any edible plant part or tissue enabling bacterial colonization can be used according to the teachings of the present invention. According to certain embodiments, the edible plant part is selected from the group consisting of leaf, fruit, root, tuber, bulb, stem, seed and any combination thereof.

According to certain exemplary embodiments, the edible plant part comprises prebiotic components. According to some embodiments, the prebiotic components include dietary soluble and/or insoluble fibers, including, for example, fructo-oligosaccharide. According to certain embodiments, the fructo-oligosaccharides are selected from the group consisting of, but not limited to, inulin, lactulose, and resistant starch. According to certain additional or alternative embodiments, the edible plant part comprises at least one of β-carotene, ascorbic acid, riboflavin, folic acid, iron, calcium, manganese, phosphorous, zinc and any combination thereof. According to certain additional or alternative embodiments, the edible plant part is low in calories.

According to certain embodiments, the edible plant part is a plant fresh produce harvested from the plant. According to additional exemplary embodiments, the tissue is a fresh tissue derived from a freshly harvested edible plant part.

According to certain embodiments, the edible plant part or tissue derived therefrom is dried. Any method as is known in the art to dry the edible plant part without negatively affecting the viability of the probiotic bacteria colonized therein can be used according to teachings of the present invention.

It is to be explicitly understood that the edible plant part or the tissue derived therefrom are not fermented.

According to certain exemplary embodiments, the edible plant part is a leafy produce of the plant, including, but not limited to, lettuce, spinach, endive, chard and arugula.

According to certain embodiments, the probiotic bacteria are gram positive bacteria. According to certain embodiments, the probiotic bacteria are gram negative bacteria. According to some embodiments, the probiotic bacteria are of a genus selected from the group consisting of *Enterococcus, Bifidobacterium, Lactobacillus, Propionobacterium, Bacillus, Streptococcus, Pediococcus, Escherichia, Leuconostoc*, and any combination thereof. Each possibility represents a separate embodiment of the present invention.

According to certain embodiments, the probiotic bacteria are of a species selected from the group consisting of *Enterococcus faecalis, Bifidobacterium lactis, Bifidobacterium bifidum, Lactobacillus acidophilus, Lactobacillus paracasei, Lactobacillus salivarius, Lactobacillus rhamnosus, Lactobacillus casei* B, *Bacillus subtilis* and any combination thereof. Each possibility represents a separate embodiment of the present invention.

According to certain exemplary embodiments, the probiotic bacteria are of a species selected from the group consisting of *Enterococcus faecalis, Lactobacillus paracasei, Lactobacillus acidophilus, Lactobacillus salivarius*, and any combination thereof. Each possibility represents a separate embodiment of the present invention.

According to certain embodiments, the edible plant part enriched with the colonized probiotic bacteria or the tissue derived therefrom is coated with a suitable agent and or formulation providing for a delayed release of the bacteria. According to certain exemplary embodiments, the coating comprises enteric coating protecting the plant tissues from the acidic pH of the stomach. Once the entering coating is dissolved in the intestine, the edible plant tissues are amenable to digestion by microbiota already present in the intestine and the delivered probiotic bacteria are released. According to certain embodiments, the edible plant part or tissue derived therefrom is coated with enteric coating when the probiotic bacteria are beneficially active in the intestine.

The present invention discloses for the first time that an edible plant part or a tissue derived therefrom coated with enteric coating can be used for oral delivery of a biologically active ingredient present therein, wherein the active ingredient reaches the intestine in its active form. The enteric coating prevents digestion of the edible plant tissue within the stomach, and thus prevents exposure of the biologically active ingredient to the acidic, harmful pH of the stomach. Upon elevation of the pH in the intestine, the entering coating is dissolved, exposing the plant tissue to digestion and release of the active ingredient stored therein.

Thus, according to additional aspect, the present invention provides an edible plant part or a tissue derived therefrom comprising at least one biologically active agent, coated with enteric coating.

According to certain embodiments, the biologically active agent is probiotic bacteria. According to some embodiments, the coated edible plant part or tissue derived therefrom further comprises at least one additional active agent selected from the group consisting of a nutritionally active agent, a therapeutically active agent and a combination thereof. According to certain embodiments, the additional active agent is a by-product of the presence of the probiotic bacteria.

Any enteric coating agent or combination of agents known in the art to be resistant to the acidic pH of the stomach of non-ruminant mammals and to be dissolved in the higher pH of the intestine can be used according to the teachings of the present invention. According to certain exemplary embodiments, the enteric coating comprises Cellulose Acetate Phthalate (CAP).

According to additional aspect, the present invention provides a method for oral delivery of probiotic bacteria to a subject in need thereof, the method comprising orally administering to the subject an effective amount of an edible plant part or a tissue derived therefrom enriched with probiotic bacteria of at least one species, wherein the probiotic bacteria are capable of inhabiting the gastrointestinal (GI) tract of said subject.

According to additional aspect, the present invention provides an edible plant part or a tissue derived therefrom enriched with probiotic bacteria of at least one species, wherein the probiotic bacteria are capable of inhabiting the gastrointestinal (GI) tract of said subject for use in a method for oral delivering to a subject an effective amount of the probiotic bacteria.

The edible plant part or tissue enriched with the probiotic bacteria are as described hereinabove.

According to certain embodiments, the edible plant part or tissue derived therefrom enriched with at least one colonized probiotic bacterial species is coated with enteric coating.

According to certain embodiments, the probiotic bacteria reach the subject intestine. According to some embodiments, the probiotic bacteria propagate in the subject intestine.

According to certain embodiment, the method results in altering the subject gastrointestinal microbiota profile compared to the profile before administering to said subject the edible plant part or tissue derived therefrom enriched with the at least one probiotic bacterial species.

According to yet additional or alternative embodiments, the method results in a beneficial therapeutic effect. According to certain embodiments, the therapeutic effect comprises treating or preventing GI-related disease or disorder.

An initial bacteria load of $10^7$ CFU/g is recommended for probiotic food, for example, yogurt. The high numbers have been suggested to compensate for the possible loss in the numbers of the probiotic bacteria during passage through the stomach and intestine. Preferably, even a higher bacteria load of $10^{10}$ CFU/g of yogurt is used to ensure delivery of a greater number of live probiotic bacteria to the target sites, e.g. small intestines and colon. The plant-based delivery vehicle of the present invention may enable several magnitude lower load of the probiotic bacteria, as the plant tissue provide the bacteria both with protection through the GI passage and initial energy source at the site of activity, enabling immediate proliferation of the probiotic bacteria at the site of action.

According to yet additional or alternative embodiments, the method results in a beneficial cosmetic effect. According to certain embodiments, the cosmetic effect comprises regulation of skin appearance. According to some embodiments, skin appearance regulation includes, but is not limited to, reduction of skin acne, reduction of skin flaking and reduction of signs of skin aging. Each possibility represents a separate embodiment of the present invention.

According to certain embodiments, the subject is a non-ruminant mammal. According to certain exemplary embodiments, the subject is human.

The edible plant part, tissue derived therefrom, the probiotic bacteria and the entering coating are as described hereinabove.

According to additional aspect, the present invention provides a method for selecting and/or producing probiotic bacterial species having endophytic characteristics of being capable of growing in a plant tissue, the method comprising:
  a) applying to a plant or a part thereof an effective amount of at least one species of probiotic bacteria known to only inhabit animal gastrointestinal tract;
  b) growing the plant or part thereof under conditions enabling augmentation of at least one leaf and/or emergence of at least one new leaf;
  c) isolating bacteria from the at least one augmented and/or newly emerged leaf;
  d) identifying the isolated bacteria; and
  e) selecting bacteria of the probiotic species applied in step (a) or strains derived thereof, said probiotic bacteria are capable of growing in a plant.

According to certain embodiments, the method is repeated at least once as to confirm the capability of the selected probiotic bacteria to colonize in a plant.

It is to be explicitly understood that the method of the present invention for selecting probiotic bacterial species capable of colonizing plant tissues encompasses isolating bacteria from augmented leaf a week after inoculation and/or from newly developed plant tissues that are not directly inoculated with the probiotic bacteria. Thus, only bacteria that can survive, propagate and spread within the plant tissue are selected, optimizing the selection of probiotic bacteria to be used according to the teachings of the present invention.

The selected probiotic bacteria capable of colonizing a plant tissue can be identical to the bacteria strain initially applied to the plant or part thereof, or can exhibit modified characteristics and thus be identified as modified strain or even as a new strain of bacteria, with the proviso that the modified or new strain exhibit probiotic characteristics.

According to another aspect, the present invention provides a method for producing an edible plant part enriched with at least one probiotic bacteria species capable of inhabiting the gastrointestinal (GI) tract of an animal, the method comprising:
  a. applying to a plant or a part thereof the at least one bacteria species;
  b. growing the plant or part thereof to obtain a plant producing the edible plant part; and
  c. harvesting the edible plant part, said edible plant part is enriched with the at least one bacterial species.

According to certain embodiments, the method further comprises the steps of:
  i. isolating the at least one bacterial species from the leaves or stem of the plant of step (b);
  ii. propagating the isolated at least one bacteria species of step (i);
  iii. applying the propagated bacteria of step (ii) to a plant or a part thereof; and
  iv. repeating step (b).

According to certain embodiments, steps (i)-(iii) are repeated at least once.

According to certain embodiments, the plant part is selected from the group consisting of seeds, stems and leaves. Each possibility represents a separate embodiment of the present invention. According to certain exemplary embodiments, the plant part is a seed.

Any method as is known in the art for applying the at least one probiotic bacterial species to the plant or part thereof can be used according to the teachings of the present invention. According to certain exemplary embodiments, the at least one probiotic bacterial species is suspended in a liquid. According to certain embodiments, the liquid is water. According to other embodiments, the liquid is a culture medium. According to certain embodiments, the liquid is applied to the plant or part thereof by a method selected from the group consisting of infiltration, immersion/dipping, incubation, spraying, and any combination thereof. Each possibility represents a separate embodiment of the present invention.

According to certain embodiments, the plant part is a seed. According to certain embodiments, the at least one probiotic bacterial species is applied to the seed via seed coating. According to certain exemplary embodiments, a plurality of seeds is coated with a seed coating agent comprising the at least probiotic bacterial species. According to these embodiments, a plurality of plants is grown from the plurality of seeds.

It is to be understood that any combination of each of the aspects and the embodiments disclosed herein is explicitly encompassed within the disclosure of the present invention.

Other objects, features and advantages of the present invention will become clear from the following description and drawings.

Figure 5:
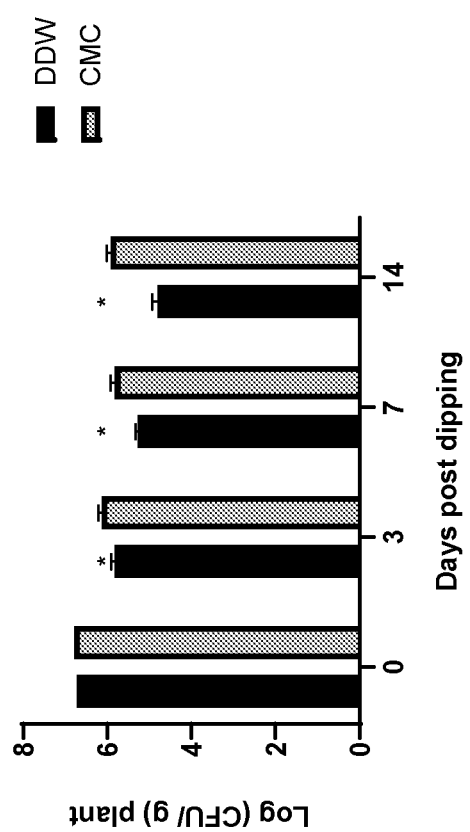

FIG. 5 demonstrates the survival of *Enterococcus faecalis* bacteria applied to lettuce cut leaves by dipping the leaves in a solution comprising the bacteria with or without CMC. *indicate significant differences (p<0.05); error bars represent standard error of the mean (n=10).

DETAILED DESCRIPTION OF THE INVENTION

Gut probiotics are live microbes that beneficially affect an animal host by modulating mucosal and systemic immunity, as well as improving intestinal function and microbial balance in the gastrointestinal tract. Various nutritional and therapeutic effects have been ascribed to probiotics including: modulating immune response, lowering serum cholesterol concentrations, improving lactose intolerance symptoms, increasing resistance to infectious intestinal diseases, decreasing duration of diarrhea, reducing blood pressure, and helping to prevent colon cancer. In order to exert their beneficial effects on the host, probiotics must remain viable and reach the intestine in large numbers.

The present invention provides a platform technology providing plant material that is a vehicle for orally delivering beneficial probiotic bacterial species to the gastrointestinal tract, and particularly to the intestine of a non-ruminant animal subject in need thereof. The plant material is typically fresh produce which by itself provides healthy food ingredients including dietary fibers, vitamins, micro- and macronutrients. According to certain embodiments, the plant part is leafy fresh produce, which is also low in calories. Furthermore, the plant material comprises prebiotic ingredients that induce the growth or activity of the probiotic bacteria once reaching the subject gastrointestinal tract.

All plants are inhabited internally by diverse microbial communities comprising bacterial, archaeal, fungal, and protistic taxa. Bacteria are associated with plants in various ways, part of which leading to plant diseases and damage to the plant life, but part having beneficial effects on the plant growth and characteristics. Endophytic bacteria are generally defined as bacteria colonizing plants without causing visible harm. Endophytic bacteria benefits from their host plant, receiving a constant food supply and being sheltered from environmental stress. In exchange, bacterial endophytes may offer several benefits to the host plant, particularly growth promotion in terms of increased germination rates, biomass, leaf area, chlorophyll content, nitrogen and protein content, hydraulic activity, yield and tolerance to abiotic stresses. Some endophytes protect their host plant from pathogens and can act as biocontrol agents.

Definitions

The terms "endophyte" and "endophytic" with reference to bacteria refers to bacteria capable of colonizing plants without causing visible harm to the plant. Endophytic bacteria can be obligate endophytes, i.e. bacteria that live within plant tissues for the entirety of its life cycle or facultative (transient), i.e. bacteria which may spend only part of the life cycle within the plant.

The terms "probiotic bacteria", "gut probiotic bacteria", and "probiotic bacteria capable of inhabiting the gastrointestinal (GI) tract of an animal" are used herein interchangeably and refer to non-pathogenic bacteria that beneficially affect a non-ruminant animal subject by improving the intestinal microbial balance. In some embodiments, the probiotic bacteria have therapeutic beneficial effect in preventing and/or treating a disease or disorder. In some embodiments, the probiotic bacteria have a nutritional beneficial effect. In yet additional embodiments, the probiotic bacteria improve the general well-being of the subject consuming same.

The term "prebiotic" as used herein is directed to compounds (for example, dietary compounds in food) that can induce or aid with the growth or activity of probiotic microorganism. In some examples, a prebiotic is a substrate that is selectively used by a microorganism, or selectively affect the microorganism. According to the teachings of the present invention, the prebiotic is an edible plant tissue or a compound derived therefrom.

As used herein, the terms "exogenously applied" and "intentionally applied" refer to the application of isolated gut probiotic bacteria of at least one species, or of an agricultural composition comprising same. It is to be explicitly understood that the probiotic bacteria to be applied are enriched with the desired isolate species or plurality of species. Accordingly, application of agricultural compositions contaminated with probiotic bacteria (for example manure used for fertilization, manure-contaminated irrigation water) is referred to herein as unintentional application and is specifically excluded from the teachings of the present invention.

The terms "colony forming unit" and CFU (in single or plural) are used herein interchangeably as an indicative number of viable bacteria.

The terms "comprise", "comprises", "comprising", "includes", "including", "having" and their conjugates mean "including but not limited to".

As used herein the term "about" in reference to a numerical value stated herein is to be understood as the stated value +/−10%.

As used herein, the singular form "a", "an" and "the" include plural references unless the context clearly dictates otherwise. For example, the term "a compound" or "at least one compound" may include a plurality of compounds, including mixtures thereof.

According to one aspect, the present invention provides an edible plant part or a tissue derived therefrom enriched with probiotic bacteria of at least one species colonizing the edible plant part or tissue derived therefrom, wherein the probiotic bacteria are capable of inhabiting the gastrointestinal (GI) tract of an animal.

The edible plant part or tissue may be enriched with one genus and/or species and/or strain of probiotic bacteria or with a combination thereof. According to the teachings of the present invention the probiotic bacteria are gut bacteria, i.e. bacteria found in the gut microbiome of a non-ruminant animal. In some embodiments, the plant part or tissue may be enriched with various species or strains present at equal amounts or at different amounts, at equal or different proportions.

The present invention is based in part on the application of isolated probiotic bacteria enriched for selected species or plurality of species to a plant or a part thereof which results in the enrichment of an edible part of the plant with the probiotic bacteria species or plurality of species.

According to certain embodiments, the at least one probiotic bacteria species comprise at least 15%, at least 16%, at least 17%, at least 18%, at least 19%, at least 20%, at least 21%, at least 22%, at least 23% at least 24% at least 25% at least 26% at least 27% at least 28% at least 29% at least 30% or more of the total bacteria species colonizing the edible plant part or tissue derived therefrom.

According to certain embodiments, the edible plant part or tissue derived therefrom comprises at least $10^4$ colony forming units (CFU) of the probiotic bacteria per gram of the edible plant part or tissue derived therefrom.

According to certain embodiments the edible plant part or tissue derived therefrom comprises from about $10^4$ CFU/g plant tissue to about $10^{11}$ CFU/g plant tissue or any subranges thereof. According to certain embodiments, the amount of probiotic bacteria can range from about $10^4$ CFU/g to about $5\times10^{10}$ CFU/g, or from about $10^4$ CFU/g to about $10^9$ CFU/g, or from about $10^6$ CFU/g to about $5\times10^9$ CFU/g. According to certain exemplary embodiments, the amount of probiotic bacteria ranges from about $10^4$ CFU/g plant tissue to about $10^8$ CFU/g plant tissue.

According to certain embodiments, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% by weight of the edible plant part or tissue derived therefrom comprises at least $10^5$ CFU of the probiotic bacteria per gram of the edible plant part or tissue derived therefrom.

According to certain embodiments, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% by weight of the edible plant part or tissue derived therefrom comprises at least $10^6$ CFU of the probiotic bacteria per gram of the edible plant part or tissue derived therefrom.

The terms "colony forming unit" and "CFU" are used herein interchangeably in its broadest meaning in the art. According to certain embodiments, the CFU of the at least one probiotic bacterial species is a bacterial cell in an active state. According to certain embodiments the CFU of the at least one probiotic bacterial species is in a dormant state selected from the group consisting of a bacterial spore, a bacterial cyst and a bacterial resting-cell.

According to certain exemplary embodiments, the at least one probiotic bacteria species has not been previously demonstrated to colonize plant tissues, and thus are define as non-endophytic bacteria.

According to certain embodiments, the probiotic bacteria are of endophytic bacteria species capable of naturally colonizing a plant. According to these embodiments, the concentration of the enriched probiotic bacteria in the edible plant part or tissue is higher compared to the concentration of the same probiotic bacteria in a corresponding edible plant part of a control plant. The control plant is a plant to which the probiotic bacteria were not intentionally applied at any growth stage. The control plant may harbor naturally occurring probiotic bacteria without the intervention according to the present invention, but at a lower amount and/or at a different species composition and/or at a different species proportions.

According to certain aspects, the present invention provides methods for selecting and/or producing probiotic bacterial species capable of colonizing in plants. The present invention further provides methods for enriching an edible plant part or tissue with the probiotic bacteria that acquired the capability to grow and proliferate within plant tissues.

As described hereinabove, probiotics as functional food components should demonstrate diverse properties. Importantly, no adverse effects may be associated with the presence of the bacterial species in the animal body. The majority of bacteria belonging to the *Lactobacillus* and *Bifidobacterium* genera are recognized as safe and beneficial as probiotics. *Lactobacillus* and *Bifidobacterium* genera are normal residents of the microbiota in the human gastrointestinal tract, in which they develop soon after birth. It is generally accepted that, with the only exception of streptococci and enterococci, lactic acid bacteria are rarely pathogenic to humans and animals. Specific strains of *Enterococcus, E. faecium* and *E. faecalis* are the only enterococci used as probiotics or feed additives (Franz C M et al., 2011. Int. J. Food Microbiol. 151, 125-140). These bacteria have been used in production of foods since ancient times with no negative effects on humans (Grajek, W. et al., Present. Int. Rev. Conf. Biotechnol, 2004). It is surmised that probiotic bacteria positively affect the human health through a wide variety of different putative mechanisms. They involve the reinforcement of the intestinal barrier, alterations of the immune response, and development of antagonism to pathogens either by the production of antimicrobial compounds or throughout competitive activities towards mucosal binding sites (Ouwehand, A. C. et al., Int. Dairy J. 9, 43-52, 1999).

Any bacterial species and/or strain known to have a beneficial probiotic activity when present in the gastrointestinal tract of a non-ruminant mammal, particularly human subject can be used according to the teachings of the present invention.

According to certain embodiments, the probiotic bacteria are gram positive bacteria. According to certain embodiments, the probiotic bacteria are gram negative bacteria. Several genera of bacteria are known to have probiotic activity (Fijan S. International journal of environmental research and public health 11(5), 4745-4767, 2014). According to some embodiments, the probiotic bacteria are of a mammal not pathogenic genus selected from the group consisting of *Enterococcus, Bifidobacterium, Lactobacillus, Propionobacterium, Bacillus, Streptococcus, Pediococcus Escherichia, Leuconostoc*, and any combination thereof. Each possibility represents a separate embodiment of the present invention.

According to certain embodiments, the probiotic bacteria are of the species *Enterococcus faecalis*.

According to certain embodiments, the probiotic bacteria are of the species, *Lactobacillus paracasei*.

According to certain embodiments, the probiotic bacteria comprises a combination of *Enterococcus faecalis* and *Lactobacillus paracasei*. According to certain embodiments, the method of the present invention for selecting and/or producing probiotic bacterial species capable of growing in a plant comprises the following steps:

a) applying to a plant or a part thereof an effective amount of at least one species of gut probiotic bacteria;
b) growing the plant or part thereof under conditions enabling augmentation of at least one leaf and/or emergence of at least one new leaf;
c) isolating bacteria from the at least one augmented and/or newly emerged leaf;
d) identifying the isolated bacteria; and
e) selecting bacteria of the probiotic species applied in step (a) or strains derived therefrom, said probiotic bacteria are capable of growing in a plant.

According to certain embodiments, the plant part is selected from the group consisting of seeds and leaves.

According to certain exemplary embodiments, the method is repeated at least once as to confirm the capability of the selected probiotic bacteria to grow in a plant, specifically to colonize the intercellular and intracellular space of the plant tissues.

Any method as is known in the art for applying the at least one probiotic bacterial species to the plant or part thereof can be used according to the teachings of the present invention. According to certain exemplary embodiments, the at least one probiotic bacterial species is suspended in a liquid. According to certain embodiments, the liquid is applied to the plant or part thereof by a method selected from the group consisting of infiltration, immersion/dipping, incubation, spraying, and any combination thereof. Each possibility represents a separate embodiment of the present invention.

According to certain embodiments, the plant part is a seed. According to certain embodiments, the at least one probiotic bacterial species is applied to the seed via seed coating. According to certain exemplary embodiments, a plurality of seeds is coated with a seed coating formulation comprising the at least probiotic bacterial species. According to these embodiments, a plurality of plants is grown from the plurality of seeds.

Any seed coating formulation compatible for bacterial growth can be used according to the teachings of the present invention. According to some embodiments, the seed coating formulation comprises at least one adherent selected from the group consisting of carboxymethyl cellulose, alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Gum Ghatti, and polyoxyethylene-polyoxybutylene block copolymers. Each possibility represents a separate embodiment of the present invention. According to certain exemplary embodiments, the coating formulation comprises carboxymethyl cellulose.

The method of the present invention for selecting probiotic bacteria encompasses selection of the bacteria from plant part(s) or tissues not necessarily directly inoculated. This type of selection is of high significance, as the selected bacteria can survive, propagate and spread within the plant tissues, indicating valid endophytic characteristics.

It is to be explicitly understood that the bacteria selected at step (e) may be identical to the bacteria applied to the plant or part thereof at step (a), or the selected bacteria may comprise genetic variation compared to the bacteria first applied. According to these embodiments, modified or new sub-strains may be produced.

Only bacterial species capable of surviving and/or proliferating in a plant tissue and having beneficial probiotic characteristics can be used according to the teachings of the present invention. Accordingly, the probiotic characteristic of the modified or new sub-strains are examined, using any suitable model as is known in the art. According to certain embodiments, a mice model system is used to validate the probiotic characteristics of the modified or new sub-strain.

According to certain aspects, the present invention provides an edible plant part or a tissue derived therefrom enriched with at least one probiotic bacterial species selected or produced according to the method of the invention.

According to another aspect, the present invention provides a method for producing an edible plant part enriched with at least one probiotic bacteria species capable of inhabiting the gastrointestinal (GI) tract of an animal, the method comprising:
 a. applying to a plant or a part thereof the at least one bacteria species;
 b. growing the plant or part thereof to obtain a plant producing the edible plant part; and
 c. harvesting the edible plant part, said edible plant part is enriched with the at least one bacterial species.

According to certain embodiments, the method further comprises the steps of:
 i. isolating the at least one bacterial species from the leaves or stem of the plant of step (b);
 ii. propagating the isolated at least one bacteria species of step (i);
 iii. applying the propagated bacteria of step (ii) to a plant or a part thereof; and
 iv. repeating step (b).

According to certain embodiments, steps (i)-(iii) are repeated at least once.

The plant part to which the probiotic bacteria are applied and the methods of application are as described hereinabove.

As described hereinabove, the present invention harnesses the phenomenon of endophytic bacteria to provide a superior vehicle for oral delivery of probiotic bacteria to non-ruminant animal, particularly to humans.

The plant provides the probiotic endophytic bacteria with the environmental conditions required for the bacteria colonization and propagation. The colonized probiotic bacteria are delivered to the subjects within edible parts of the plant, typically fresh, such that there is no need to take any special measures to keep the probiotic bacteria alive until consumption. Furthermore, the plant tissues protect the probiotic bacteria, providing a sort of an encapsulation, such that significant number of viable probiotic bacteria reach their site of action. Accordingly, even relatively low number of the probiotic bacteria present in the edible plant part results in an effective number within the GI of the subject consuming same.

Furthermore, plant fresh produce (including fruit, vegetables, tubers, bulbs and leafy produce) are the most important raw-eaten food worldwide and are a substantial part of a balanced and healthy diet. Many beneficial effects on health and lifestyle are attributed to the consumption of fresh-cut or minimally processed edible plant products as they represent a good source of vitamins, e.g. β-carotene, ascorbic acid, riboflavin and folic acid as well as minerals, e.g. iron, calcium, manganese and phosphorous. Moreover, plant fresh produce is known to be rich sources of micronutrients as well as dietary fiber, particularly in leafy produce, enabling the intake of these nutrients. Finally, the relatively low amount of carbohydrates and fats, particularly in vegetables and leafy foods correlates with a low calorie value, making them leading candidates for healthy diet. In addition, the presence of non-digestible or low-digestible food ingredient characterizes plant fresh produce as prebiotic substance, stimulating the growth or activity of beneficial probiotic bacteria in the human colon (Biedrzycka B., Polish J. food Nutr. Sci. 13, 143-150, 2004).

According to certain embodiments, the probiotic bacteria are present at a site selected from the group consisting of the edible plant part or tissue intercellular space, the edible plant part or tissue intracellular space and a combination thereof. According to some embodiments, the prebiotic bacteria are further present on the edible plant part or tissues surface. According to certain exemplary embodiments, the probiotic bacteria are colonized within the intercellular and/or intracellular space.

According to certain embodiments, the edible plant part comprises the at least one probiotic bacterial species actively growing. According to other embodiments, the edible plant part comprises the at least one probiotic bacterial species in its dormant form.

According to certain embodiments, the edible plant part is selected from the group consisting of leaf, stem, fruit, root, tuber, bulb, seed and any combination thereof.

According to certain exemplary embodiments, the edible plant part is rich in dietary fibers. According to certain additional or alternative embodiments, the edible plant part is rich in prebiotic components. According to certain additional or alternative embodiments, the edible plant part is rich in at least one of β-carotene, ascorbic acid, riboflavin, folic acid, iron, calcium, manganese, phosphorous, zinc and any combination thereof. According to certain additional or alternative embodiments, the edible plant part is low in calories.

According to certain exemplary embodiments, the edible plant part is a leafy produce of the plant.

According to certain exemplary embodiments, the probiotic bacteria are of a species selected from the group consisting of *Lactobacillus acidophilus, Lactobacillus paracasei, Lactobacillus salivarius, Enterococcus faecalis*, and any combination thereof. Each possibility represents a separate embodiment of the present invention.

As described hereinabove, additional advantage of the plant-derived edible vehicle of probiotic bacteria of the present invention is that the plant tissues provide protection to the probiotic bacteria from unfavorable environmental conditions and further at least partial protection to the bacteria through the transit via the stomach to the intestine.

To further protect the probiotic bacteria, the present invention now discloses coating the edible plant part or tissue derived therefrom with a suitable coating to obtain a delayed release of the probiotic bacteria, so as to avoid exposure of the probiotic bacteria to the acidic pH of the stomach. As used herein the term "delayed release" refers to a time delay between oral administration of the edible plant part or tissue enriched with the probiotic bacteria and the release of said bacteria from the plant part or tissue. "Delayed release" may or may not involve gradual release of the probiotic bacteria over an extended period of time, and thus may or may not be "sustained release".

According to certain embodiments, the coating is enteric coating.

Enteric-coated formulations are suitable vehicles for modification of the release of drug or active agent at specific target areas within the gastrointestinal tract. Enteric coating is an effective method of protecting the drug or agent against a gastric environment and preventing its release before reaching the target site. Therefore, enteric polymer-coated formulations have been developed to prevent acid degradation in the stomach. In addition, the enteric coating must be readily soluble in alkaline buffer so that the drug or active agent is readily available for systemic absorption. Enteric polymers can be divided into three categories: (i) modified cellulosic derivatives e.g., cellulose acetate phthalate, hypromellose phthalate, hypromellose acetate succinate and (ii) methyl acrylate-methacrylic acid copolymers and (iii) other materials e.g., Shellac, polyvinyl acetate phthalate (Caillard, R. et al., Int. J. Pharm. 499, 321-329, 2016).

Cellulose acetate phthalate (CAP) has been used as an enteric coating material due to its non-ionized form which predominates in acid but becomes soluble once the phthalic acid groups become ionized above pH 6 (Balamuralidhara, V. et al., Am. J. drug Discov. Dev. 1, 24-48, 2011). CAP contains about 35% phthalyl and 24% acetyl groups (U.S. Pat. Nos. 4,960,814 and 5,025,004). It has been described that one carboxyl of the phthalic acid is combined with cellulose, and the other is free for further reactions. The resulting polymeric acid forms water-soluble alkaline salts. CAP was further clinically tested and was demonstrated not to have toxic effects, and to be remarkably inert as a compound of the diet. Moreover, there is no evidence in the laboratory and manufacturing handling of this product to indicate any allergenic or sensitizing effects (Hodge, H. C. J. Pharmacol. Exp. Ther. 80, 1944). Recent studies by Sachdeva et al. have been performed on the production of enteric-coated biochanin A microparticles and their pharmacological potential was investigated in hypertensive ovariectomized rats (Ovx-HT) (Sachdeva, C. et al., Drug Deliv. 23, 2044-205, 2016). The authors concluded that the enteric-coating of biochanin A exhibited delayed release capacity, an increase in oral bioavailability up to 6 folds than plain biochanin A and antihypertensive effect in ovariectomized rats possibly in an eNOS dependent manner Other studies have reported that the CAP coated oral tablet formulations successfully enabled the delivery of drug to the intestine where the alkaline environment dissolves the protective coating (Sachdeva, et al., 2016, ibid; Bertz, A. et al., J. Biotechnol. 163, 243-249, 2013; Wong, C. Y. et al., J. Pharm. Pharmacol. 69, 285-294, 2017).

According to certain aspects, the present invention provides an edible plant part or a tissue derived therefrom comprising a biologically active agent, coated with enteric coating.

The present invention encompasses coated edible plant parts or tissues comprising any biologically active agent that can habitat the edible plant part or be expressed therein. According to certain embodiments, the biologically active ingredient is selected from the group consisting of a nutritionally active agent, a therapeutically active agent and a combination thereof.

According to certain embodiments, the biologically active agent is endogenous to the edible plant part. According to other embodiments, the biologically active agent is heterologous to the edible plant part.

According to certain embodiments, the biologically active agent is probiotic bacteria.

According to certain additional or alternative embodiments, the biologically active agent is selected from the group consisting of a protein, a polynucleotide, a vitamin, a chemotherapeutic agent, an anti-oxidant, an anti-aging agent.

According to additional aspect, the present invention provides a food product comprising a plant tissue enriched with at least one probiotic bacterial species according to the teachings of the invention or a lysate thereof.

According to yet additional aspect, the present invention provides an oral formulation comprising a plant tissue enriched with the at least one probiotic bacterial species according to the teachings of the invention or a lysate thereof.

The plant tissue can be in a form selected from the group consisting of intact tissue, cut tissue, grinded tissue, and any combination thereof. Typically, the plant tissue is fresh, but may be present in other forms including frozen and dried form, as long as the probiotic bacteria preserve the ability to propagate once reaching a subject intestine.

Any food product or an oral formulation as is known in the art can be used according to the teachings of the present invention.

According to certain embodiments, the oral formulation is a liquid formulation selected from the group consisting of suspensions, elixirs and solutions. According to certain embodiments, the oral formulation is a solid formulation selected from the group consisting of powders, tablets, capsules and pills.

The plant tissue and the probiotic bacteria are as described hereinabove.

According to additional aspects, the present invention provides a method for oral delivery of at least one species of gut probiotic bacteria to a subject in need thereof, the method comprising orally administering to the subject an effective amount of an edible plant part or a tissue derived therefrom enriched with the gut probiotic bacteria.

According to further aspects, the present invention provides an edible plant part or a tissue derived therefrom enriched with at least one gut probiotic bacteria species for use in oral delivery of an effective amount of the probiotic bacteria to a subject.

According to further aspects, the present invention provides use of an edible plant part or a tissue derived therefrom enriched with at least one gut probiotic bacteria species for oral delivery of the probiotic bacteria.

According to certain embodiments, the edible plant part or tissue derived therefrom enriched with at least one probiotic bacteria species is coated with enteric coating.

According to certain embodiments, the probiotic bacteria reach the intestine of a subject consuming the plant or part thereof. According to some embodiments, the probiotic bacteria propagate in the subject intestine.

According to certain embodiments, oral delivery of the edible plant part or tissue enriched with the probiotic bacteria results in altering the gastrointestinal microbiota profile of a subject consuming the edible plant part or tissue compared to the profile before consumption.

According to certain embodiments, oral delivery of the edible plant part or tissue provides a beneficial therapeutic effect to the subject.

According to certain embodiment's, the therapeutic effect comprises comprising treating or preventing GI-related disease or disorder.

Oral administration of the edible plant part or tissue enriched with probiotic bacteria according to the teachings of the present invention may have a therapeutic effect in treating and/or preventing gastrointestinal tract related diseases or disorder, including, but not limited to diarrhea, diarrhea caused by antibiotic, arthritis, obesity, irritable bowel syndrome (IBS), cancer, heartburn, offset lactose intolerance; chronic fatigue syndrome and other forms of suffering from an unbalanced bacterial population in the intestine; in repopulation of the gut microbiome after antibiotic therapy; in inhibiting pathogenic bacteria; in supporting the immune system; in reducing cholesterol; in enhancing the bio-availability of calcium, zinc, iron, manganese, copper and phosphorus; and in synthesis of vitamins. Non-limiting examples of a subject receiving and benefiting from such an oral administration include a non-ruminant mammal including human or a domestic animal or a farm animal such as cats, dogs, pigs, poultry or fish.

According to certain embodiments, oral delivery of the edible plant part or tissue provides a beneficial cosmetic effect to the subject.

According to yet another aspect, the present invention provides a cosmetic method comprising topically administering to a subject in need thereof a plant tissue enriched with at least one probiotic bacteria species or a lysate thereof. It is to be explicitly understood that the lysate comprises a cosmetically effective amount of the probiotic bacteria. The lysate can be prepared by any method as is known in the art.

The at least one probiotic bacterial species is as described hereinabove.

According to certain embodiments, the subject is a non-ruminant mammal.

According to certain exemplary embodiments, the subject is a human.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Selecting Introduced Probiotic Bacteria with Endophytic Characteristics Several probiotic bacteria species known to be capable of growing in the GI of an animal and have health beneficial effects were selected to be introduced into plant tissues. *Enterococcus faecalis, Lactobacillus paracasei, Lactobacillus acidophilus, Lactobacillus salivarius, Streptococcus thermophiles* and *Bacillus subtilis*, belonging to different bacterial families, were purchased from ATTC and grown in culture in optimal conditions (Lactobacilli MRS agar (BD Difco), supporting growth of all lactobacilli; or Brain Heart Infusion (BHI, BD Difco) agar, general-purpose medium for the growth of a wide variety of bacteria, at 37° C.). Each bacteria species was collected from the agar plate and re-suspended in PBS to achieve a final concentration of $10^6$ CFU/ml.

Leaf Inoculation

A bacterial culture of *Lactobacillus paracasei* obtained as described hereinabove was infiltrated into leaves of lettuce plantlets at a volume of about 1 ml (culture O.D=0.1 at 600 nm). After infiltration the plants were grown in growth chamber at 27° C. with long day period of 12 hours of light.

After 10 days, samples (leaf pieces) from the infiltrated leaf and from new emerging leaves were collected. The bacteria were extracted from each sample by grinding the leaves in PBS using a crater and pestle and directly plating the resulted mixture using serial dilutions on selective medium. The different colonies that grew in the medium were identified by sequencing of 16S rRNA gene. Table 1 shows exemplary results for the assay performed with *Lactobacillus paracasei*.

TABLE 1

Quantification and identification of probiotic strain isolated from lettuce leaf ten-days post infiltration

| Bacterial species infiltrated into lettuce plantlets | Number of CFU/ml in infiltrated lettuce leaves (percentage of inhabited leaves) | Number of CFU/ml in new emerging lettuce leaves (percentage of inhabited leaves) | 16S rRNA gene identification |
|---|---|---|---|
| *Lactobacillus paracasei* | $2.86 * 10^4$ (100%) | $7.2 * 10^3$ (66%) | *L. paracasei* |

Seed Coating

*Enterococcus faecalis, Lactobacillus paracasei*, and *Bacillus subtilis* were grown in culture in optimal conditions as described hereinabove to achieve a final concentration of $10^6$ CFU/ml. Each bacteria species was collected from the agar plate and blended with 2% carboximetilcelulose (CMC) (Song, Y et al., J. Agric. Sci. 6, 132, 2014) with vigorous shaking in order to achieve a homogenous suspension with a final concentration of $10^7$-$10^8$ CFU/ml. CMC is a food-grade substance, approved by the US Food and Drug Administration (FDA) for use in food products.

Lettuce seeds were coated with the suspension of bacteria and CMC. The coated seeds were germinated in aseptic system of Hoagland No. 2 basal salt mixture agar (pH 6.5) and grown in a Plant Growing Room set to 22° C. and long day period of 12 hours of light.

After 9 days, leaf samples of plants developed from the coated seeds were collected. The bacteria were extracted from each sample by grinding the leaves in Saline using a crater and pestle. The resulted mixture was plated on BHI agar medium. Colonies that grew on the supportive medium were identified by sequencing of 16S rRNA gene. The number of CFU/ml medium for each bacterial species is presented in Table 2 hereinbelow.

TABLE 2

Quantification and identification of probiotic strains isolated from leaves of lettuce developed from coated seeds

| Bacterial species coated onto lettuce seed | Number of CFU/ml coating solution | Number of CFU/ml in lettuce leaf | 16S rRNA gene identification |
|---|---|---|---|
| *Lactobacillus paracasei* | $5 * 10^8$ | $3.72 * 10^5$ | *L. paracasei* |
| *Enterococcus faecalis* | $12 * 10^8$ | $1.53 * 10^6$ | *E. faecalis* |
| *Lactobacillus salivarius* | $10 * 10^8$ | $2.84 * 10^4$ | *L. salivarius* |

Root Immersion in Aqueous Solution (Hydroponic Growth)

Applying gut probiotic bacteria to plants via immersion of the bacteria in hydroponic media for plant growth requires that the gut probiotic bacteria can grow in the hydroponic medium, which typically includes fertilizers. Candidate probiotic bacteria or probiotic bacteria already shown to have the capability of endophytic growth are grown to form cell culture as described hereinabove. Plant hydroponic medium is inoculated with the bacteria culture and left to grow within the medium under conditions of hydroponic plant growth as are known in the art. Medium samples are taken at several time points (4 h, 24 h and 48 h) and the number of CFU/ml is counted. Probiotic bacteria propagating in the hydroponic medium are selected.

Selected bacteria are grown to form a cell culture and added to the medium of hydroponically grown plants (e.g. lettuce). After about three and/or five days, leaf samples are taken, grinded in a buffer, and the number of CFU/leaf weight is measured as described hereinabove.

The above-described protocols are suitable for selecting and/or enriching for probiotic bacteria with endophytic growth capabilities using other plants with edible leaves, for example spinach.

Example 2: Survival of the Gut Probiotic Bacteria within the Plant Tissues

The capability of the selected bacteria colonies to enter and grow in the plant is validated by isolating the bacteria from newly developed leaves to which the bacteria were migrated; growing the selected bacteria in sterile cultures; and applying the resulted culture to new plants according to the first method applied (leaf infiltration, seed coating, or immersion). The procedure is repeated for 2-10 rounds. The results of an exemplary experiment, in which the bacteria were first applied by seed coating, are presented in Table 3 hereinbelow.

TABLE 3

Quantification and identification of probiotic strain isolated from leaves of lettuce developed from coated seeds

| No. of Enrichment Cycles | Bacteria amount in lettuce leaves (log CFU/g) | | | | | | | | | |
|---|---|---|---|---|---|---|---|---|---|---|
| | 1 | 2 | 3 | 4 | 5 | 6 | 7 | 8 | 9 | 10 |
| *Bacillus Subtilis* | 4.623 | TNTC* | 7.505 | 4.905 | 4.825 | | | | | |
| *Enterococcus Faecalis* | TNTC | 8.161 | 7.663 | TNTC | 7.297 | TNTC | 6.924 | TNTC | 7.723 | 7.053 |
| *Lactobacillus Paracasei* | 7.927 | 7.877 | 7.699 | 5.155 | 6.017 | 6.017 | 5.079 | 6.526 | 7.927 | 7.877 |

*TNTC—too numerous to count

Example 3: Endophytic Growth of the Selected Probiotic Bacteria

Probiotic bacteria that acquired endophytic characteristics (i.e. being capable of surviving and multiplying in a plant tissue at significant concentrations) selected as described hereinabove are defined as colonized bacteria having endophytic characteristics. The endophytic characteristics of the selected bacteria was examined by separating bacteria present onto the leaves (epiphytic bacteria) and bacteria present within the leaf tissue (endophytic bacteria).

Separation of Epiphyte and Endophyte Bacteria by Sonication

Figure 1:
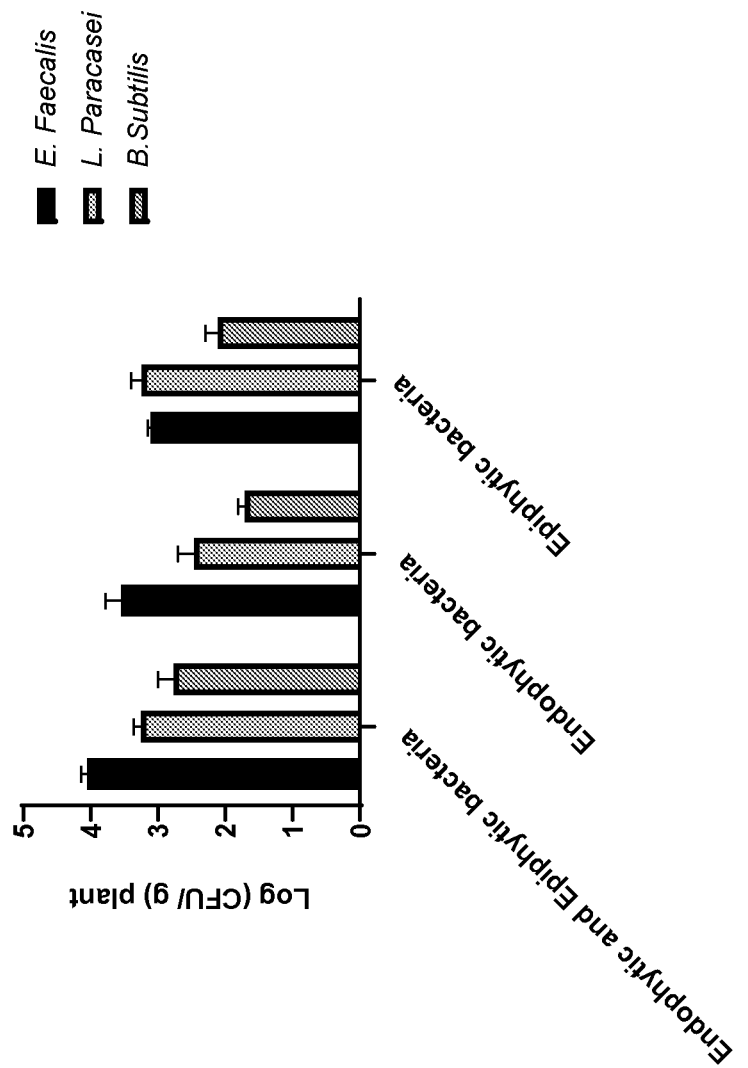
FIG. 1 shows partitioning of the introduced bacteria to epiphytes and endophytes in leaves of plantlets developed from seeds coated with carboximetilcelulose (CMC)-probiotic bacteria mixture, when separation is performed by sonication. The probiotic bacteria used were *E. Faecalis, L. Paracasei*, and *B. subtilis*. Each analysis was performed in quadruplicate; error bars represent standard error of the mean (n=4).

Lettuce seeds were coated with probiotic bacteria (*E. faecalis, L. Paracasei* or *B. subtilis*) and Carboxymethyl cellulose (CMC) solution as described hereinabove. The coated seeds were germinated in aseptic system. After 12 days, leaf samples of plants grown from the coated seeds were collected. Samples were sonicated in 900 μl sterilized saline in sonication bath (ultrasonic Elmasonic S 10/H; Frequency 50/60 H) for 7 min and then both saline (representing epiphytic bacteria) and crushed sonicated leaves (representing endophytic bacteria) were plated on supportive medium. In addition, leaves without sonication were sampled (sampling both epiphytic and endophytic bacteria). Data were subjected to one-way ANOVA, and pair-comparison of treatment means was achieved by Tukey's procedure at $P<0.05$, using a statistical software (JMP). As is shown in FIG. 1, the bacteria partitioned between the outer part and the inner tissues of the leaves in comparable concentrations. It is to be noted that detachment of tightly surface-attached bacteria by sonication enabled improved growth of these bacteria on the supportive medium compared to the growth of bacteria of the control leaves which were not subjected to sonication. Sonication has been recently shown to be an acceptable method for removing surface-attached bacteria (Richter-Heitmann T et al., 2016. Frontiers in Microbiology 7, Article 773, doi: 10.3389/fmicb.2016.00773; Qvit-Raz N et al. 2008. Genetics 178(3): 1615-1622. doi: 10.1534/genetics.107.082164; Beattie G A and Lindow S E. 1999. Phytopathology 89(5):353-9. doi: 10.1094/PHYTO.1999.89.5.353).

Example 4: Characteristics of Colonized Probiotic Bacteria

In order to ensure that bacteria acquired endophytic characteristics did not lose their probiotic characteristics, colonized bacteria isolate of *E. Faecalis, L. Paracasei*, and *B. subtilis* were examined. The examined bacteria were isolated from lettuce leaves of plants after seven cycles of seed coating (with culture each of the bacteria species)—plant growth—isolation of bacteria from the plant leaves, confirming the endophytic growth characteristics of the bacteria.

The isolated bacteria were grown in solutions simulating gastric fluid (SGF, containing 2 grams of NaCl; 3.2 g pepsin (Sigma; and 80 mL of 1 M HCl; mixed together to make 1 L with distilled water). In one experiment, the effect of acidic pH (pH−2 and pH=4) was examined, using SGF containing pepsin. The experiment was conducted as follows:

Original isolates of the above-described probiotic bacteria (i.e. isolates not subjected to growth cycles in plant tissues) were used as a control. Bacteria (test and control) were harvested after 18 h growth in BHI or MRS or NB (Nutrient broth, Millipore)—medium culture by centrifugation (5,000×g, 10 min, 4° C.) and washed twice with PBS (pH 7.2). 1 mL of the cell suspensions (free cells) was gently mixed with 10 mL of sterile simulated gastric juice and resuspended in 10 ml of SGF pre-warmed to 37° C. The cell suspensions were incubated for 120 min at 37° C. in aerobic condition under stirring (≈200 rpm). Samples were taken at 0, 30, 60, 120 min and plated on BHI\MRS\NB agar. Survival was examined by counting the number of CFUs, wherein the number of CFU at time 0 taken as a control.

Figure 2A:
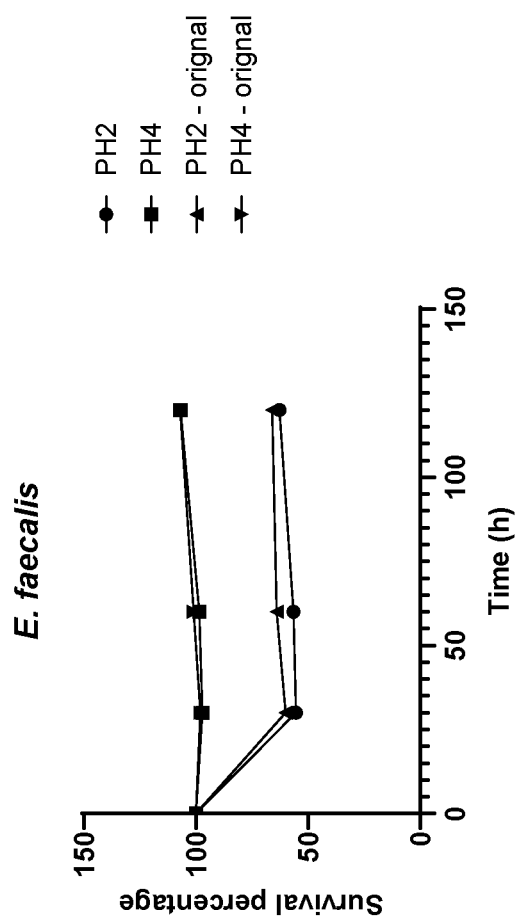
FIG. 2 shows the survival percentage of original probiotic isolates of *E. Faecalis* (FIG. 2A), *L. Paracasei* (FIG. 2B), and *B. subtilis* (FIG. 2C) [obtained from the American Type Culture Collection (ATCC) bank] compared to the survival percentage of same isolate species isolated from lettuce plant (after 7 growth cycles) exposed to solution simulating gastric fluid (SGF) containing Pepsin at pH=2 or pH=4.
Figure 2B:
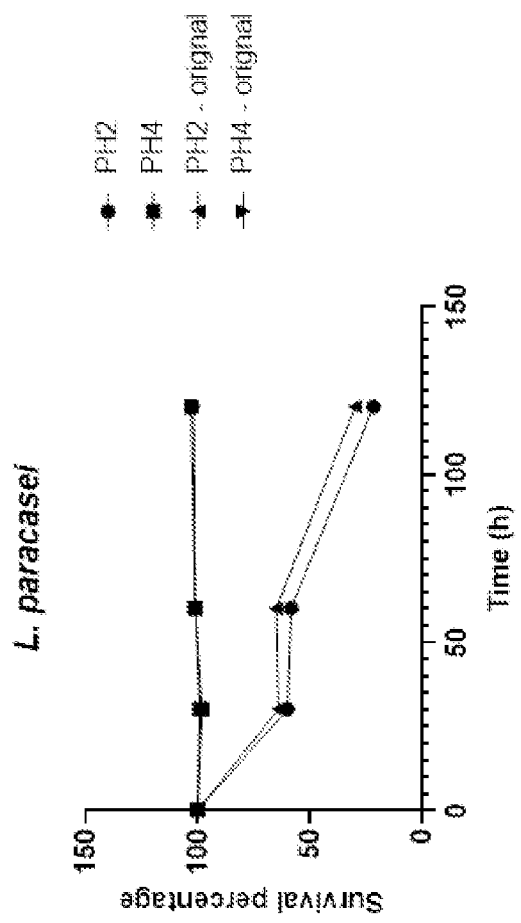
Figure 2C:
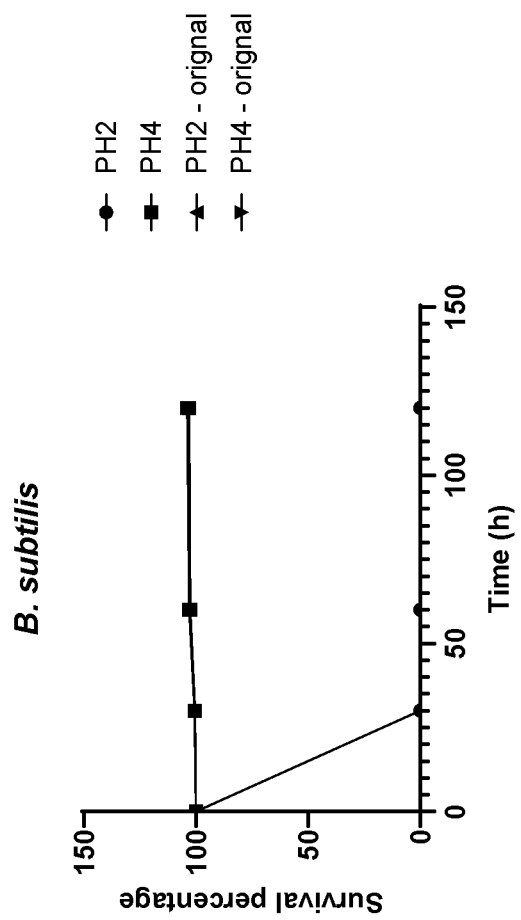

As is shown in FIG. 2, no significant differences could be observed in the survival rate of the bacteria acquired endophytic characteristics compared to the original probiotic isolates.

Figure 3:
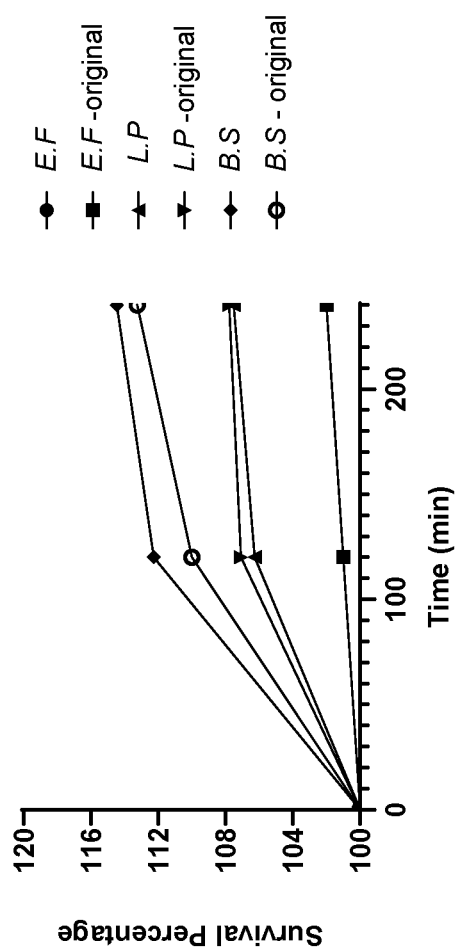
FIG. 3 shows the survival percentage of original (obtained from ATCC bank) probiotic isolates of *E. faecalis* (EF), *L. paracasei* (LP), and *B. subtilis* (BS) compared to the survival percentage of same isolate species isolated from lettuce plant (after 7 growth cycles) exposed to solution simulating intestinal fluid (SIF) containing pancreatic enzymes for 120 or 240 min at 37° C. and at pH=6.8.

In another experiment, the effect of a solution simulating intestinal fluid (SIF) containing pancreatic enzymes was examined (SIF: 6.8 g of monobasic potassium phosphate, 1 g of Pancreatine (Sigma) and 77 ml of 0.2N NaOH mixed together to make 1 L with distilled water. pH of the solution was corrected to pH 6.8 by adding 0.2N NaOH). Probiotic bacteria as above (colonized bacteria that acquired endophytic characteristics and original isolates) were grown essentially as described above, resuspending the harvested cell in SIF. The cell cultures were incubated for 4 h at 37° C. in aerobic condition under stirring (≈200 rpm). Samples were taken at 0, 120, 240 min., plated on BHI\MRS\NB agar and survival rate was measured. Each assay was performed in triplicates. As for the solutions simulating gastric fluid, the colonized exogenic bacteria isolated showed similar survival rate is solution simulating intestinal fluid compared to the original isolates (FIG. 3). These results clearly demonstrate that colonizing the probiotic bacteria in plant tissue conferring to the probiotic bacteria endophytic characteristics had no adverse effect of the bacteria essential probiotic characteristics of resistance to the harsh environment of the gastrointestinal tract.

Example 5: Survival of the Introduced Bacteria

Figure 4:
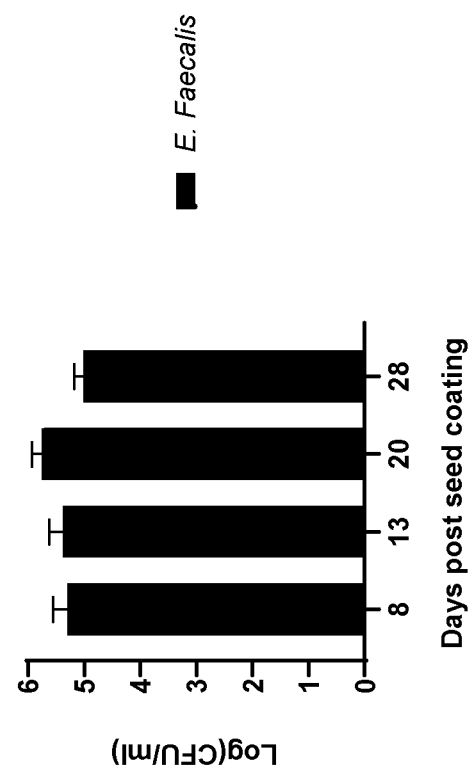
FIG. 4 shows *E. Faecalis* establishment in lettuce leaves of plant developed from coated seeds after 8, 13, 20 and 28 days. Each analysis was performed in quadruplicate. error bars represent standard error of the mean (n=4).

Lettuce seeds were coated with carboxymethyl cellulose (CMC) containing *E. Faecalis* (originated from cycle 10). The coated seeds were germinated in aseptic system of Hoagland No. 2 basal salt mixture agar (pH 6.5). Leaves, originating from plants germinated from the coated seeds, were sampled 8, 13, 20 and 28 days after sowing (plantlets were immersed around day 4). The bacteria were extracted from each sample by crushing the leaves in Saline and plating it on supportive medium. Colonies that grew on the supportive medium were identified by sequencing of 16S rRNA gene. Data were subjected to one-way ANOVA, and pair-comparison of treatment means was achieved by Tukey's procedure at $P<0.05$, using a statistical software (JMP). No significant difference in the bacteria amounts was observed during 28 days of growth (FIG. 4).

Example 6: Coating Plant Vegetative Tissues with Enteric Coating

*Enterococcus faecalis* bacteria were collected from agar plate and blended with two different solutions: double distilled water (DDW) and 2% carboximetilcelulose (CMC). The final concentration of the *E. faecalis* bacteria was $10^6$ CFU/ml. To form bacteria-CMC suspension, the solution was vigorously shaken until homogenous suspension was obtained Lettuce cut leaves were dipped in each of the two different bacterial solutions for 10 minutes. The coated leaves were kept in a sterile box in the refrigerator at 4° C.

After 3, 7 and 14 days, the bacteria were extracted from each sample by crushing the leaves in DDW and directly plating the mixture using serial dilutions on supportive medium. Untreated leaves (leaves not subjected to bacterial solution) served as control, and no probiotic bacteria were found in these leaves in all experiments. The different colonies that grew in the medium were identified by sequencing of 16S rRNA gene. Each analysis was performed in ten repeats. Data were subjected to one-way ANOVA, and pair-comparison of treatment means was achieved by Tukey's procedure at $P<0.05$, using a statistical software (JMP). FIG. 5 demonstrates that CMC protected the bacteria present in the leaves while not interfering with its growth, as significantly higher number of CFU was detected when the leaves were dipped in a solution comprising CMC.

Example 7: Viability and Survival of Probiotic Bacteria in the GI of Mice Consuming Vegetative Tissues Enriched with the Probiotic Bacteria Mice (male C57BL/6JOLAHSD mice 8 weeks old) are fed for two consecutive days with three different diets:

Control group (1): diet containing regular mice food (5 mice);

Control group (2): diet containing regular mice food mixed with regular lettuce (5 mice);

Test group: diet containing regular mice food mixed with lettuce enriched with the probiotic bacteria *Enterococcus faecalis* according to the teachings of the present invention (5 mice).

Each mouse from control group 2 and the test group is fed with 1 g lettuce per day for two consecutive days. From the third day onwards, all groups are fed with regular mice food only.

Stool from all mice is collected every day at the beginning of the dark phase, and immediately snap-frozen and transferred for storage at $-80°$ C. until further processing. DNA is isolated from stool samples, using Power Soil Kit (QIAGEN) and the presence of *E. faecalis* in the stool is determined by q-PCR analysis of *E. faecalis* 16S rRNA and EDA-2 gene (Peykov S Z et al. 2012. Mol Biol Rep 39, 7025-7030. DOI 10.1007/s11033-012-1533-z).

Mice are sacrificed on the fourth day, and contents of several parts of the gastrointestinal tract, especially from the colon and cecum are collected. Presence of *E. faecalis* in the intestinal contents is determined by q-PCR analysis. The colon undergo fixation in order to detect putative probiotic survival by FISH methodology (Chassaing B et al., 2015. Nature. 519(7541), 92-6. doi: 10.1038/nature14232; Johansson M E et al., 2012. Methods Mol Biol. 842, 229-35. doi: 10.1007/978-1-61779-513-8_13).

Example 8: Effect of Consumption of Vegetative Tissues Enriched with Probiotic Endophytic Bacteria of Some Embodiments of the Invention on Intestinal Inflammation The effect of plant vegetative tissues enriched with probiotic endophytic bacteria according to the teachings of the invention on prevention and/or treatment of intestinal inflammation is examined with mouse model of IBD induced by dextran sodium sulfate (DSS). The preventive or treatment protocol is performed essentially as previously described (Avram-Hananel, L., et al., Dis. Colon Rectum 53, 1676-1686, 2010). Non-treated mice are used as negative control and mice treated with the same species of isolated microbiotic endophytic bacteria are used as a positive control.

Example 9: Production of Plant Fresh Produce Enriched with Probiotic Bacteria

*Enterococcus faecalis* and optionally also of *Lactobacillus paracasei*, are grown on agar of a respective medium overnight at a temperature of $28°$ C. Bacteria colonies are then picked and re-suspended in DDW containing 2% CMC to reach turbidity (OD at 600 nm=0.15). Solution containing $10^7$ cfu/ml is taken for application.

Lettuce plants are used as an example of fresh leafy produce. Lettuce plants (n=50) are grown under field conditions as is known in the art. About 5 days before harvest, 30 plants are sprayed with the bacteria-CMC solution. 20 plants serve as a control.

After 5 days, all plants are harvested, and the lettuce leaves are washed with sterile DDW. Samples are taken from each plant (100 g tissue per sample). From each group (treated and control plant), 20-25 random samples are taken directly after the wash with DDW; 5-10 random samples are sonicated to detach epiphytic bacteria as described hereinabove; and 5-10 additional random samples are surface sterilized by at least one method (with ethanol, hypochlorite sodium (NaOCl) or a combination thereof).

All samples are then crushed in sterile DDW and plated on a respective medium. Number of CFU/g tissue is calculated. Number of CFU/g identified in the sonicated and/or surface sterilized samples indicate endophytic bacteria.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An edible fresh produce comprising:
    an edible plant part or a tissue derived therefrom comprising at least one strain of probiotic bacteria colonizing an intercellular space and/or intracellular space of the edible plant part or tissue derived therefrom, being a result of exogenous inoculation of a pre-harvested plant with said at least one strain of probiotic bacteria and growth of the inoculated pre-harvested plant,
    wherein said at least one strain of probiotic bacteria is not a natural endophyte of said edible fresh produce and has acquired endophytic characteristics comprising the capability to grow and proliferate in the inoculated pre-harvested plant from which said edible plant part or tissue derived therefrom is derived,
    wherein said edible fresh produce is selected from the group consisting of a leafy produce, a root, a tuber, and a bulb of the plant,
    wherein said at least one strain of probiotic bacteria is capable of inhabiting the gastrointestinal (GI) tract of an animal, and wherein said at least one strain of probiotic bacteria maintains or improves health of said animal.

2. The edible fresh produce according to claim 1, wherein the edible plant part or tissue derived therefrom comprises at least $10^4$ colony forming units (CFUs) of the probiotic bacteria per gram.

3. The edible fresh produce according to claim 1, wherein at least 80% by weight of the edible plant part or tissue derived therefrom comprises at least $10^5$ CFUs of the probiotic bacteria per gram.

4. The edible fresh produce according to claim 1, wherein the at least one strain of probiotic bacteria is not a natural endophyte species of a plant tissue.

5. The edible fresh produce according to claim 4, wherein the at least one strain of probiotic bacteria is a plant endophyte and wherein the concentration of the at least one strain of probiotic bacteria in the edible plant part or tissue is higher compared to the concentration of the same at least one strain of probiotic bacteria in a corresponding edible plant part of a control plant, and wherein the control plant is a plant to which the at least one strain of probiotic bacteria were not intentionally applied at any growth stage.

6. The edible fresh produce according to claim 1, wherein the edible plant part or tissue comprises at least one prebiotic component.

7. The edible fresh produce according to claim 1, wherein the at least one strain of probiotic bacteria are of a genus being selected from the group consisting of: *Enterococcus, Bifidobacterium, Lactobacillus, Propionibacterium, Bacillus, Streptococcus, Pediococcus, Escherichia, Leuconostoc,* and any combination thereof.

8. The edible fresh produce according to claim 1, wherein the edible plant part or tissue is coated with a coating material providing for delayed release of the at least one strain of probiotic bacteria from said edible plant part or tissue.

9. The edible fresh produce according to claim 8, wherein the coating material comprises at least one enteric coating component.

10. An edible plant part or a tissue derived therefrom being derived from the edible fresh produce of claim 1, being in a dried form.

11. The edible fresh produce according to claim 1, wherein said edible plant part or a tissue derived therefrom is enriched with said probiotic bacteria, wherein the concentration of the enriched probiotic bacteria in the edible plant part or tissue derived therefrom is higher compared to the concentration of the same probiotic bacteria in a corresponding edible plant part or tissue derived therefrom of a control plant.

12. The edible plant part of claim 11, wherein said control plant is a plant to which the probiotic bacteria were not exogenously applied at any growth stage.

13. The edible fresh produce according to claim 1, wherein said at least one strain of probiotic bacteria is live bacteria.

14. The edible fresh produce according to claim 1, wherein the at least one strain of probiotic bacteria comprises at least 15% of the total endophytic bacteria colonizing the edible plant part or tissue derived therefrom of said edible fresh produce.

15. The edible fresh produce of according to claim 1, wherein said leafy produce comprises any one of: lettuce, spinach, endive, chard, and arugula.

16. The edible fresh produce according to claim 1, wherein the probiotic bacteria having acquired endophytic characteristics is capable of withstanding surface sterilization of said edible fresh produce.

17. The edible fresh produce according to claim 1, wherein said plant tissue is an intact tissue.

18. The edible fresh produce according to claim 1, wherein said probiotic bacteria maintain or improve structure and/or function of a recipient gastrointestinal bacterial population at a healthy or to a healthier state.

19. The edible fresh produce according to claim 1, being suitable for correcting or reducing the effect of dysbiosis.

* * * * *